US008293684B2

(12) United States Patent
Mouritzen et al.

(10) Patent No.: US 8,293,684 B2
(45) Date of Patent: Oct. 23, 2012

(54) LOCKED NUCLEIC ACID REAGENTS FOR LABELLING NUCLEIC ACIDS

(75) Inventors: Peter Mouritzen, Jyllinge (DK); Christian Lomholt, Frederiksberg (DK); Søren Morgenthaler Echwald, Humlebæk (DK); Mikkel Noerholm, Belmont, MA (US)

(73) Assignee: Exiqon, Vedbaek (DK)

( * ) Notice: Subject to any disclaimer, the term of this patent is extended or adjusted under 35 U.S.C. 154(b) by 1033 days.

(21) Appl. No.: 11/947,724

(22) Filed: Nov. 29, 2007

(65) Prior Publication Data

US 2009/0023594 A1    Jan. 22, 2009

Related U.S. Application Data (60) Provisional application No. 60/861,633, filed on Nov. 29, 2006.

(51) Int. Cl.
*C12Q 1/68* (2006.01)
*C12M 1/34* (2006.01)
*C12M 3/00* (2006.01)
*C07H 21/04* (2006.01)
*C07H 19/20* (2006.01)
*C07H 21/02* (2006.01)

(52) U.S. Cl. ......... 506/9; 536/23.1; 536/26.6; 435/6.11; 435/287.1

(58) Field of Classification Search .................. None
See application file for complete search history.

(56) References Cited

U.S. PATENT DOCUMENTS

| | | | |
|---|---|---|---|
| 3,687,808 A | 8/1972 | Merigan et al. |
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,357,421 A | 11/1982 | Emtage et al. |
| 4,366,241 A | 12/1982 | Tom et al. |
| 5,143,854 A | 9/1992 | Pirrung et al. |
| 5,215,899 A | 6/1993 | Dattagupta |
| 5,242,974 A | 9/1993 | Holmes |
| 5,252,743 A | 10/1993 | Barrett et al. |
| 5,324,633 A | 6/1994 | Fodor et al. |
| 5,384,261 A | 1/1995 | Winkler et al. |
| 5,412,087 A | 5/1995 | McGall et al. |
| 5,424,186 A | 6/1995 | Fodor et al. |
| 5,432,272 A | 7/1995 | Benner |
| 5,437,990 A | 8/1995 | Burg et al. |
| 5,451,683 A | 9/1995 | Barrett et al. |
| 5,466,586 A | 11/1995 | Davey et al. |
| 5,482,867 A | 1/1996 | Barrett et al. |
| 5,491,074 A | 2/1996 | Aldwin et al. |
| 5,523,221 A | 6/1996 | Weiner |
| 5,527,681 A | 6/1996 | Holmes |
| 5,541,061 A | 7/1996 | Fodor et al. |
| 5,550,215 A | 8/1996 | Holmes |
| 5,571,639 A | 11/1996 | Hubbell et al. |
| 5,578,832 A | 11/1996 | Trulson et al. |
| 5,593,839 A | 1/1997 | Hubbell et al. |
| 5,599,695 A | 2/1997 | Pease et al. |
| 5,624,711 A | 4/1997 | Sundberg et al. |
| 5,631,734 A | 5/1997 | Stern et al. |
| 5,733,729 A | 3/1998 | Lipshutz et al. |
| 5,795,716 A | 8/1998 | Chee et al. |
| 5,800,992 A | 9/1998 | Fodor et al. |
| 5,831,070 A | 11/1998 | Pease et al. |
| 5,834,758 A | 11/1998 | Trulson et al. |
| 5,837,832 A | 11/1998 | Chee et al. |
| 5,856,092 A | 1/1999 | Dale et al. |
| 5,856,101 A | 1/1999 | Hubbell et al. |
| 5,858,659 A | 1/1999 | Sapolsky et al. |
| 5,871,928 A | 2/1999 | Fodor et al. |
| 5,889,165 A | 3/1999 | Fodor et al. |
| 5,902,723 A | 5/1999 | Dower et al. |
| 5,936,324 A | 8/1999 | Montagu |
| 5,959,098 A | 9/1999 | Goldberg et al. |
| 5,968,740 A | 10/1999 | Fodor et al. |
| 5,974,164 A | 10/1999 | Chee |
| 5,981,185 A | 11/1999 | Matson et al. |
| 5,981,956 A | 11/1999 | Stern |

(Continued)

FOREIGN PATENT DOCUMENTS

EP    1 072 679    1/2001

(Continued)

OTHER PUBLICATIONS

Greenberg, Attachment of Reporter and Conjugate Groups to the 3' Termini of Oligonucleotides, 2001, Current Protocols in Nucleic Acid Chemistry, 4.5.1-4.5.19.* U.S. Appl. No. 09/536,841, Mar. 27, 2000, Fan et al.
Baird et al., "Biochemistry, Mutagenesis, and Oligomerization of DsRed, a Red Fluorescent Protein from Coral," *Proc. Natl. Acad. Sci. U.S.A.* 97:11984-11989 (2000).
Bevis et al., "Rapidly Maturing Variants of the *Discosoma* Red Fluorescent Protein (DsRed)," *Nat. Biotechnol.* 20:83-87 (2002).
Campbell et al., "A Monomeric Red Fluorescent Protein," *Proc. Natl. Acad. Sci. U.S.A.* 99:7877-7882 (2002).
Chiesa et al., "Recombinant Aequorin and Green Fluorescent Protein as Valuable Tools in the Study of Cell Signalling," *Biochem. J.* 355:1-12 (2001).
Cook, "Medicinal Chemistry of Antisense Oligonucleotides-Future Opportunities," *Anti-Cancer Drug Des.* 6:585-607 (1991).
Danscher et al., "Autometallographic Silver Amplification of Colloidal Gold," *J. Histotechnol.* 16:201-207 (1993).
England et al., "Specific Labeling of 3' Termini of RNA with T4 RNA Ligase," *Meth. Enzymol.* 65:65-74 (1980).

(Continued)

*Primary Examiner* — Amber D Steele
*Assistant Examiner* — Lianko Garyu
(74) *Attorney, Agent, or Firm* — Clark & Elbing LLP; Kristina Bieker-Brady (57) ABSTRACT

The present invention relates to labeling kits containing novel non-natural nucleotide monomers and to methods of making and using such compounds. The invention further relates to a method of detecting the presence of a nucleic acid, e.g., RNA, of interest in a sample, the method having the following steps: providing the sample; ligating a nucleic acid of interest with a labeling reagent according to the instant invention; providing a nucleic acid array having probes directed to the nucleic acid of interest; hybridizing the labeled nucleic acid fragments to said nucleic acid array; and determining the extent of hybridization to said probes to determine the presence of the nucleic acid of interest.

28 Claims, 1 Drawing Sheet

U.S. PATENT DOCUMENTS

| | | | |
|---|---|---|---|
| 6,013,449 | A | 1/2000 | Hacia et al. |
| 6,020,135 | A | 2/2000 | Levine et al. |
| 6,025,601 | A | 2/2000 | Trulson et al. |
| 6,033,860 | A | 3/2000 | Lockhart et al. |
| 6,040,138 | A | 3/2000 | Lockhart et al. |
| 6,040,193 | A | 3/2000 | Winkler et al. |
| 6,043,060 | A | 3/2000 | Imanishi |
| 6,045,996 | A | 4/2000 | Cronin et al. |
| 6,066,454 | A | 5/2000 | Lipshutz et al. |
| 6,090,555 | A | 7/2000 | Fiekowsky et al. |
| 6,136,269 | A | 10/2000 | Winkler et al. |
| 6,141,096 | A | 10/2000 | Stern et al. |
| 6,147,205 | A | 11/2000 | McGall et al. |
| 6,177,248 | B1 | 1/2001 | Oliner et al. |
| 6,185,030 | B1 | 2/2001 | Overbeck |
| 6,185,561 | B1 | 2/2001 | Balaban et al. |
| 6,188,783 | B1 | 2/2001 | Balaban et al. |
| 6,197,506 | B1 | 3/2001 | Fodor et al. |
| 6,201,639 | B1 | 3/2001 | Overbeck |
| 6,218,803 | B1 | 4/2001 | Montagu et al. |
| 6,223,127 | B1 | 4/2001 | Berno |
| 6,225,625 | B1 | 5/2001 | Pirrung et al. |
| 6,229,911 | B1 | 5/2001 | Balaban et al. |
| 6,262,216 | B1 | 7/2001 | McGall |
| 6,268,490 | B1 | 7/2001 | Imanishi et al. |
| 6,269,846 | B1 | 8/2001 | Overbeck et al. |
| 6,284,460 | B1 | 9/2001 | Fodor et al. |
| 6,300,063 | B1 | 10/2001 | Lipshutz et al. |
| 6,303,315 | B1 * | 10/2001 | Skouv ............................ 435/6 |
| 6,308,170 | B1 | 10/2001 | Balaban |
| 6,309,822 | B1 | 10/2001 | Fodor et al. |
| 6,310,189 | B1 | 10/2001 | Fodor et al. |
| 6,333,179 | B1 | 12/2001 | Matsuzaki et al. |
| 6,344,316 | B1 | 2/2002 | Lockhart et al. |
| 6,361,947 | B1 | 3/2002 | Dong et al. |
| 6,391,592 | B1 * | 5/2002 | Su et al. ...................... 435/91.1 |
| 6,428,752 | B1 | 8/2002 | Montagu |
| 6,582,938 | B1 | 6/2003 | Su et al. |
| 6,670,461 | B1 | 12/2003 | Wengel et al. |
| 6,794,499 | B2 | 9/2004 | Wengel et al. |
| 6,872,529 | B2 | 3/2005 | Su |
| 6,965,020 | B2 | 11/2005 | McGall et al. |
| 7,524,942 | B2 | 4/2009 | Wang et al. |
| 2004/0009487 | A1 * | 1/2004 | Kadushin et al. ................ 435/6 |
| 2005/0272075 | A1 * | 12/2005 | Jacobsen et al. ................ 435/6 |
| 2011/0123991 | A1 | 5/2011 | Hoser |

FOREIGN PATENT DOCUMENTS

| | | |
|---|---|---|
| WO | WO 88/10315 | 12/1988 |
| WO | WO 90/06995 | 6/1990 |
| WO | WO 97/12896 | 4/1997 |
| WO | WO 98/39352 | 9/1998 |
| WO | WO 99/14226 | 3/1999 |
| WO | WO 99/36760 | 7/1999 |
| WO | WO 99/47964 | 9/1999 |
| WO | WO 00/56746 | 9/2000 |
| WO | WO 00/56748 | 9/2000 |
| WO | WO 00/58516 | 10/2000 |
| WO | WO 00/66604 | 11/2000 |
| WO | WO 01/00641 | 1/2001 |
| WO | WO 01/07455 | 2/2001 |
| WO | WO 01/58593 | 8/2001 |
| WO | WO 03/020739 | 3/2003 |

OTHER PUBLICATIONS

Englisch et al., "Chemically Modified Oligonucleotides as Probes and Inhibitors," in *Angewandte chemie*, International Edition in English, 30(6):613-722 (1991).

Freier et al., "The Ups and Downs of Nucleic Acid Duplex Stability: Structure-Stability Studies on Chemically-Modified DNA:RNA Duplexes," *Nucleic Acids Res.* 25:4429-4443 (1997).

Gall et al., "Formation and Detection of RNA-DNA Hybrid Molecules in Cytological Preparations," *Proc. Natl. Acad. Sci. U.S.A.* 63:378-383 (1969).

Guatelli et al., "Isothermal, In Vitro Amplification of Nucleic Acids by a Multienzyme Reaction Modeled After Retroviral Replication," *Proc. Natl. Acad. Sci. U.S.A.* 87:1874-1878 (1990).

Guckian et al., "Factors Contributing to Aromatic Stacking in Water: Evaluation in the Context of DNA," *J. Am. Chem. Soc.* 122:2213-2222 (2000).

Håkansson et al., "The Adenine Derivative of α-L-LNA (α-L-*ribo* Configured Locked Nucleic Acid): Synthesis and High-Affinity Hybridization Towards DNA, RNA, LNA and α-L-LNA Complementary Sequences," *Bioorg. Med. Chem. Lett.* 11:935-938 (2001).

Håkansson et al., "Convenient Syntheses of 7-Hydroxy-1-(Hydroxyrnethyl)-3-(thymin-1-yl)-2,5-dioxabicyclo[2.2.1] heptanes: α-L-*Ribo*- and α-L-Xylo-Configured LNA Nucleosides," *J. Org. Chem.* 65:5161-5166 (2000).

Hames and Higgins (Eds.), *Nucleic Acid Hybridization, A Practical Approach*, p. 190-193 (1985).

Hoffmann et al., "Synthesis and Reactivity of Intermediates Formed in the $T_4$ RNA Ligase Reaction," *Nucleic Acids Res.* 15:5289-5303 (1987).

Igloi, "Nonradioactive Labeling of RNA," *Anal. Biochem.* 233:124-129 (1996).

Iorio et al., "MicroRNA Gene Expression Deregulation in Human Breast Cancer," *Cancer Res.* 65:7065-7070 (2005).

John et al., "RNA-DNA Hybrids at the Cytological Level," *Nature* 223:582-587 (1969).

Ke et al., "MicroRNAs: Key Participants in Gene Regulatory Networks," *Curr. Opin. Chem. Biol.* 7: 516-523 (2003).

Knop et al., "Improved Version of the Red Fluorescent Protein (drFP583/DsRed/RFP)," *BioTechniques* 33:592-602 (2002).

Koshkin et al., "A Simplified and Efficient Route to 2'-O, 4'-C-Methylene-Linked Bicyclic Ribonucleosides (Locked Nucleic Acid)," *J. Org. Chem.* 66:8504-8512 (2001).

Kroschwitz, J.I. (Ed.), *Concise Encyclopedia of Polymer Science and Engineering*, John Wiley & Sons, p. 858-859 (1990).

Kumar et al., "The First Analogues of LNA (Locked Nucleic Acids): Phosphorothioate-LNA and 2'-Thio-LNA," *Bioorg. Med. Chem. Lett.* 8:2219-2222 (1998).

Kværnø et al., "Novel Bicyclic Nucleoside Analogue (1S,5S,6S)-6-Hydroxy-5-hydroxymethyl-1-(uracil-1-yl)-3,8-dioxabicyclo[3.2.1]octane: Synthesis and Incorporation into Oligodeoxynucleotides," *J. Org. Chem.* 66:5498-5503 (2001).

Kværnø et al., "Synthesis of Abasic Locked Nucleic Acid and Two *seco*-LNA Derivatives and Evaluation of Their Hybridization Properties Compared with Their More Flexible DNA Counterparts," *J. Org. Chem.* 65:5167-5176 (2000).

Kwoh et al., "Transcription-based Amplification System and Detection of Amplified Human Immunodeficiency Virus Type 1 with a Bead-based Sandwich Hybridization Format," *Proc. Natl. Acad. Sci. U.S.A.* 86:1173-1177 (1989).

Landegren et al., "A Ligase-Mediated Gene Detection Technique," *Science* 241:1077-1080 (1988).

Langer et al., "Enzymatic Synthesis of Biotin-labeled Polynucleotides: Novel Nucleic Acid Affinity Probes," *Proc. Natl. Acad. Sci. U.S.A.* 78:6633-6637 (1981).

Lagos-Quintana et al., "Identification of Novel Genes Coding for Small Expressed RNAs," *Science* 294:853-858 (2001).

Larrick et al., "Green Fluorescent Protein: Untapped Potential in Immunotechnology," *Immunotechnology* 1:83-86 (1995).

MiRCURY™ LNA Array Labeling Kit: Instruction Manual, p. 1-14 (Jun. 2006).

Mesmaeker et al., "Backbone Modifications in Oligonucleotides and Peptide Nucleic Acid Systems," *Curr. Opin. Struct. Biol.* 5:343-355 (1995).

Mirkin et al., "A DNA-based Method for Rationally Assembling Nanoparticles into Macroscopic Materials," *Nature* 382:607-609 (1996).

Morita et al., "2'-O,4'-C-Ethylene-Bridged Nucleic Acids (ENA): Highly Nuclease-Resistant and Thermodynamically Stable Oligonucleotides for Antisense Drug," *Bioorg. Med. Chem. Lett.* 12:73-76 (2002).

Pfundheller et al., "Evaluation of Oligonucleotides Containing Two Novel 2'-O-Methyl Modified Nucleotide Monomers: A 3'-C-Allyl and a 2'-O,3'-C-Linked Bicyclic Derivative," *Nucleosides Nucleotides* 18:2017-2030 (1999).

Richardson et al., "Biotin and Fluorescent Labeling of RNA Using T4 RNA Ligase," *Nucleic Acids Res.* 11:6167-6184 (1983).

Rosenbohm et al., "Synthesis of 2'-Amino-LNA: A New Strategy," *Org. Biomol. Chem.* 1:655-663 (2003).

Sacchetti et al., "The Molecular Determinants of the Efficiency of Green Fluorescent Protein Mutants," *Histol. Histopathol.* 15:101-107 (2000).

Sanghvi, "Heterocyclic Base Modifications in Nucleic Acids and Their Applications in Antisense Oligonucleodies," Chapter 15, in *Antisense Research and Applications*, Crooke and Lebleu (Eds.), CRC Press, 1993, pp. 273-288.

Singh et al. "Synthesis of Novel Bicyclo[2.2.1] Ribonucleosides: 2'-Amino- and 2'-Thio-LNA Monomeric Nucleosides," *J. Org. Chem.* 63:6078-6079 (1998).

Singh et al., "Synthesis of 2'-Amino-LNA: A Novel Conformationally Restricted High-Affinity Oligonucleotide Analogue with a Handle," *J. Org. Chem.* 63:10035-10039 (1998).

Terskikh et al., "Analysis of DsRed Mutants: Space Around the Fluorophore Accelerates Fluorescence Development," *J. Biol. Chem.* 277:7633-7636 (2002).

Verkhusha et al., "An Enhanced Mutant of Red Fluorescent Protein DsRed for Double Labeling and Developmental Timer of Neural Fiber Bundle Formation," *J. Biol. Chem.* 276:29621-29624 (2001).

Wang et al., "Direct and Sensitive miRNA Profiling From Low-Input Total RNA," *RNA* 13:151-159 (2007).

Wu et al., "The Ligation Amplification Reaction (LAR)-Amplification of Specific DNA Sequences Using Sequential Rounds of Template-Dependent Ligation," *Genomics* 4:560-569 (1989).

Latorra et al., "Design considerations and effects of LNA in PCR primers," *Molecular and Cellular Probes*. 17: 253-259 (2003).

Di Giusto and King, "Strong positional preference in the interaction of LNA oligonucleotides with DNA polymerase and proofreading exonuclease activities: implications for genotyping assays," *Nucleic Acids Research*.32(3): e32 1-8 (2004).

Kaur et al.,"Perspectives on Chemistry and Therapeutic Applications of Locked Nucleic Acid (LNA)," *Chem Rev.* 107:4672-4697 (2007).

Psifidi et al., "Novel Quantitative Real-Time LCR for the Sensitive Detection of SNP Frequencies in Pooled DNA: Method Development, Evaluation and Application," *PLos One.* 6(1): e145600 1-11 (2011).

\* cited by examiner

SEQUENCE LISTING

```
<160> NUMBER OF SEQ ID NOS: 8

<210> SEQ ID NO 1
<211> LENGTH: 24
<212> TYPE: RNA
<213> ORGANISM: Homo sapiens

<400> SEQUENCE: 1
guccaguuuu cccaggaauc ccuu                                              24

<210> SEQ ID NO 2
<211> LENGTH: 23
<212> TYPE: RNA
<213> ORGANISM: Homo sapiens

<400> SEQUENCE: 2
gugccuacug agcugauauc agu                                               23
```

```
<210> SEQ ID NO 3
<211> LENGTH: 21
<212> TYPE: RNA
<213> ORGANISM: Homo sapiens

<400> SEQUENCE: 3
uagguaguuu cauguuguug g                                              21

<210> SEQ ID NO 4
<211> LENGTH: 23
<212> TYPE: RNA
<213> ORGANISM: Homo sapiens

<400> SEQUENCE: 4
uacccuguag auccgaauuu gug                                            23

<210> SEQ ID NO 5
<211> LENGTH: 22
<212> TYPE: RNA
<213> ORGANISM: Homo sapiens

<400> SEQUENCE: 5
aauacugccg gguaaugaug ga                                             22

<210> SEQ ID NO 6
<211> LENGTH: 23
<212> TYPE: RNA
<213> ORGANISM: Homo sapiens

<400> SEQUENCE: 6
aaaagcuggg uugagagggc gaa                                            23

<210> SEQ ID NO 7
<211> LENGTH: 24
<212> TYPE: RNA
<213> ORGANISM: Homo sapiens

<400> SEQUENCE: 7
aaaagugcuu acagugcagg uagc                                           24

<210> SEQ ID NO 8
<211> LENGTH: 20
<212> TYPE: RNA
<213> ORGANISM: Homo sapiens

<400> SEQUENCE: 8
cauaaaguag aaagcacuac                                                20
```

LOCKED NUCLEIC ACID REAGENTS FOR LABELLING NUCLEIC ACIDS

CROSS-REFERENCE TO RELATED APPLICATIONS

This application claims benefit of U.S. Provisional Application No. 60/861,633, filed Nov. 29, 2006, which is hereby incorporated by reference.

FIELD OF THE INVENTION

This invention relates to nucleic acid labelling reagents. These labelling reagents have a detectable moiety or moieties, which allow a nucleic acid to be detected with an appropriate test. More specifically, the invention relates to nucleic acid labelling compounds that can be used to label the 3' end of an RNA molecule

BACKGROUND OF THE INVENTION

Gene expression in diseased and healthy cells and in cells in different stages of development is often different. The ability to monitor gene expression in such cases provides researchers and medical professionals with a powerful diagnostic tool. One can monitor gene expression, for example, by measuring the presence or absence of a nucleic acid (e.g., a mRNA) that is the transcription product of a gene of interest. Monitoring the nucleic acid may be accomplished by chemically or biochemically labelling the mRNA with a detectable moiety followed by hybridization to a nucleic acid probe for the gene. The detection of a labelled nucleic acid at the probe position indicates that the targeted gene has been expressed.

Various methods of RNA detection have been developed. These include the "Northern" blotting procedure and the use of radioactive isotopes such as $^{32}P$. Non-radioactive detection techniques have also been developed. Langer et al., Proc. Natl. Acad. Sci. USA 1981, 78, 6633-6637, for example, disclosed certain biotin labelled nucleosides. Lockhart et al., U.S. Pat. No. 6,344,316, disclosed enzymatic methods of end-labelling with non-radioactive nucleotides. Igloi et al, Anal. Biochemistry, 233, 124-9, 1996, disclosed methods for non-radioactive labelling of RNA. Wang et al, RNA (2007), 13, 1-9, disclosed methods for a microRNA profiling assay.

There remains, however, a need for nucleic acid, e.g., RNA, labelling reagents that can be used for efficient and accurate labelling and monitoring of gene expression.

SUMMARY OF THE INVENTION

The invention relates to nucleic acid labelling reagents and methods of their use. These labeling reagents have a detectable moiety or moieties, which allow a nucleic acid to be detected with the appropriate equipment or test. Nucleases, specifically RNA-targeting nucleases (i.e., RNAses), can cause non-specific degradation of RNA and constitute an important problem in isolating and handling of RNA preparations. Provided in this invention is a labelling reagent including LNA nucleotides which may confer increased nuclease resistance to the target RNA so labelled. This may reduce the risk of sample degradation during sample handling and processing.

Accordingly, in one aspect, the invention features a nucleic acid labelling reagent having the formula:

or an ion thereof,
wherein B is a nucleobase, e.g., 5-methylcytosine; $R^2$ is a functional group that permits attachment to a 3' OH group of a nucleic acid, e.g., $PO_4^{2-}$, or an acid thereof, L is a linker group, e.g., $C_{1-10}$-alkyl amino, wherein the amino group is bound to $R^1$; and $R^1$ is a detectable moiety, e.g., biotin or a cyanine dye (such as Cy3, Cy5, Oyster-556, or Oyster-656). In one embodiment, L is —$(CH_2)_6NH$—, wherein the amino group is bound to $R^1$, and $R^2$ is $PO_4^{2-}$, or an acid thereof.

The invention also features a method of detecting the presence of a nucleic acid of interest by providing a sample having nucleic acid which may or may not be a nucleic acid of interest; ligating nucleic acid in the sample to a labelling reagent of the invention; providing a collection of detection probes directed to the nucleic acid of interest; contacting the labelled nucleic acids with the collection under hybridizing conditions, e.g., stringent conditions; and determining the extent of hybridization of the labelled nucleic acids to the detection probes to determine the presence of the nucleic acid of interest. It will be understood that, for any given target nucleic acid, a plurality of probes having the same sequence may be present in the collection, and/or a plurality of probes having different sequences but still hybridizing to the target nucleic acid may be present. The nucleic acid is, for example, RNA, such as miRNA. The ligating step may be catalyzed by T4 RNA ligase. The collection is for example a nucleic acid array. In certain embodiments, the collecting is immobilized onto a solid support, e.g., a bead or glass bead, where each detection probe is present at a specified location on the support. It will be understood that when beads are employed, an individual bead may only contain one probe sequence. Beads may also have a characteristic that provides for identification (e.g., fluorophore, size, color, charge, or any other identifiable signal or modification). Furthermore, although the detection probes, as defined herein, include at least one high affinity nucleotide analog, e.g., LNA, the detecting methods may also be used with collections of probes that do not include such an analog, e.g., unmodified nucleic acids.

The information obtained from detection may then be used for any suitable purpose. For example, selecting an organism out of a population based upon detection of the target nucleic acid. When the target nucleic acid is derived from a patient, e.g., a human patient, selecting a treatment, diagnosing a disease, or diagnosing a genetic predisposition to a disease, may be based upon detection of the target nucleic acid.

The methods may also further include the step of quantifying the amount of target nucleic acid in the sample, e.g., for gene express profiling. In other embodiments, the nucleic acids in the sample are contacted with a phosphatase, e.g., calf intestinal alkaline phosphatase, to remove 3' phosphate groups prior to the ligating step. The phosphatase may be employed after nucleic acids in the sample have been fragmented, as is described herein. In other embodiments, an adjuvant, e.g., DMSO or PEG, is added prior to ligation.

The invention further features a nucleic acid labelled via the 3' oxygen with a reagent of the invention.

The invention also features a kit including a reagent of the invention, a ligase, and optionally a nucleic acid array, e.g., including LNA.

As used in this application, the singular form "a," "an," and "the" include plural references unless the context clearly dictates otherwise. For example, the term "an agent" includes a plurality of agents, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

A "nucleic acid array" refers to a multiplicity of different nucleic acids attached (preferably through a single terminal covalent bond) to one or more solid supports where, when there is a multiplicity of supports, each support bears a multiplicity of nucleic acids. The term "array" can refer to the entire collection of nucleic acids on the support(s) or to a subset thereof. The spatial distribution of the nucleic acids may differ between the two arrays, but, in a preferred embodiment, it is substantially the same. It is recognized that, even where two arrays are designed and synthesized to be identical, there are variations in the abundance, composition, and distribution of nucleic acids. These variations are preferably insubstantial and/or compensated for by the use of controls as described herein.

The phrase "immobilized onto a support" means bound directly or indirectly thereto including attachment by covalent binding, hydrogen bonding, ionic interaction, hydrophobic interaction, or otherwise.

The phrase "hybridizing specifically to" refers to the binding, duplexing, or hybridizing of a molecule preferentially to a particular nucleotide sequence under stringent conditions when that sequence is present in a complex mixture (e.g., total cellular DNA or RNA).

The terms "background" and "background signal intensity" refer to signals resulting from non-specific binding, or other interactions, between labelled target nucleic acids and components of a nucleic acid array (e.g., the oligonucleotide or polynucleotide probes, control probes, the array substrate, etc.). Background may also be produced by intrinsic fluorescence of the array components themselves. A single background signal intensity can be determined for the entire array, or a different background signal may intensity be calculated for one or more regions of the array. In a preferred embodiment, background is calculated as the average signal intensity for the lowest 1% to 10% of the probes in the array, or region of the array. In expression monitoring arrays (i.e., where probes are preselected to hybridize to specific nucleic acids (genes)), a different background signal intensity may be calculated for each target nucleic acid. Where a different background signal is calculated for each target gene, the background signal intensity may be calculated for the lowest 1% to 10% of the probes for each gene. One of skill in the art will appreciate that where the probes to a particular gene hybridize well and thus appear to be specifically binding to a target sequence, they should not be used in a background signal intensity calculation. Alternatively, background may be calculated as the average signal intensity produced by hybridization to probes that are not complementary to any sequence found in the sample (e.g., probes directed to nucleic acids of the opposite sense or to genes not found in the sample such as bacterial genes where the sample is of mammalian origin). Background can also be calculated as the average signal intensity produced by regions of the array that lack any probes at all.

The term "quantifying" when used in the context of quantifying nucleic acid abundances or concentrations (e.g., transcription levels of a gene) can refer to absolute or to relative quantification. Absolute quantification may be accomplished by inclusion of known concentration(s) of one or more nucleic acids (e.g., control nucleic acids such as BioB or with known amounts the target nucleic acids themselves) and referencing the hybridization intensity of unknowns with the known nucleic acids (e.g. through generation of a standard curve). Alternatively, relative quantification can be accomplished by comparison of hybridization signals between two or more genes, or between two or more treatments to quantify the changes in hybridization intensity and, by implication, transcription level.

"Sample" refers to a sample of cells, or tissue, or fluid isolated from an organism or organisms, including but not limited to, for example, skin, plasma, serum, spinal fluid, lymph fluid, synovial fluid, urine, tears, blood cells, organs, tumours, and also to samples of in vitro cell culture constituents (including but not limited to conditioned medium resulting from the growth of cells in cell culture medium, recombinant cells and cell components).

An "organism" refers to an entity living at one time, including but not limited to, for example, human, mouse, rat, *Drosophila*, *C. elegans*, yeast, *Arabidopsis thaliana*, maize, rice, zebra fish, a primate, a domestic animal, etc.

The terms "detection probe" and "detection probe sequence" refer to a nucleic acid that includes a recognition sequence complementary to an RNA or DNA target sequence, in which the recognition sequence is substituted with a high-affinity nucleotide analog, e.g. LNA, to increase the sensitivity and specificity of conventional oligonucleotides, such as DNA oligonucleotides, for hybridization to short target sequences, e.g., mature miRNAs, stem-loop precursor miRNAs, pre-miRNAs, siRNAs or other non-coding RNAs as well as miRNA binding sites in their cognate mRNA targets, mRNAs, mRNA splice variants, RNA-edited mRNAs, pi-RNA, and antisense RNAs.

"High affinity nucleotide analog" refers to a non-naturally occurring nucleotide analog that increases the "binding affinity" of an oligonucleotide probe to its complementary recognition sequence when substituted with at least one such high-affinity nucleotide analog. Preferred analogs are LNA and PNA (peptide nucleic acid). As used herein, increased binding affinity refers to a higher association constant ($K_a$) for the detection probe recognition sequence with its complement compared to that of the complementary strands of a double-stranded molecule that does not contain a high-affinity nucleotide analog in the recognition sequence. In a preferred embodiment, the association constant of the detection probe recognition sequence is higher than the dissociation constant ($K_d$) of the complementary strand of the recognition sequence in the target sequence in a double stranded molecule.

The terms "miRNA" and "microRNA" refer to 18-25 nt non-coding RNAs. They are processed from longer (ca. 75 nt)

hairpin-like precursors termed pre-miRNAs. MicroRNAs assemble in complexes termed miRNPs and recognize their targets by antisense complementarity. If the microRNAs match 100% to their target, i.e., the complementarity is complete, the target mRNA is most probably cleaved, and the miRNA acts like a siRNA. If the match is incomplete, i.e., the complementarity is partial, then the translation of the target mRNA is most probably blocked.

The terms "small interfering RNAs" and "siRNAs" refer to 21-25 nt RNAs derived from processing of linear double-stranded RNA. siRNAs assemble in complexes termed RISC (RNA-induced silencing complex) and target complementary RNA sequences for endonucleolytic cleavage. Synthetic siRNAs also recruit RISCs and are capable of cleaving complementary RNA sequences The term "piRNA" (Piwi interacting RNAs) refers to small noncoding RNAs of 26-31-nucleotides identified through their interaction with PIWI proteins.

The term "gene" refers to a locatable region of genomic sequence, corresponding to a unit of inheritance, which is associated with regulatory regions, transcribed regions, and/or other functional sequence regions.

The term "recognition sequence" refers to a nucleotide sequence that is complementary to a region within a target nucleotide sequence essential for sequence-specific hybridization between the target nucleotide sequence and the recognition sequence.

The term "detectable moiety" means a chemical species or complex of chemical species and or particles capable of being detected by various equipment and or tests (e.g., physical, chemical, electrical and/or computer based) methods of detecting the moiety when attached for example to a nucleic acid. Exemplary detectable moieties are fluorophores.

The term "nucleic acid" refers to a polynucleotide of any origin, which is a glycoside of a nucleobase, including genomic DNA or RNA, cDNA, semi synthetic DNA or RNA, or synthetic DNA or RNA. Unless otherwise noted, the term encompasses known analogs of natural nucleotides that can function in a similar manner as naturally occurring nucleotides. Nucleic acids having modified backbones are also encompassed by this term. The nucleic acid is not necessarily physically derived from any existing or natural sequence but may be generated in any manner, including chemical synthesis, DNA replication, reverse transcription or a combination thereof. "Oligonucleotide" and "polynucleotide" may be used interchangeably with "nucleic acid."

The term "nucleobase" covers the naturally occurring nucleobases adenine (A), guanine (G), cytosine (C), thymine (T) and uracil (U) as well as non-naturally occurring nucleobases such as xanthine, diaminopurine, 8-oxo-$N^6$-methyladenine, 7-deazaxanthine, 7-deazaguanine, $N^4,N^4$-ethanocytosine, $N^6,N^6$-ethano-2,6-diaminopurine, 5-methylcytosine (also termed "mC"), 5-($C^3$—$C^6$)-alkynyl-cytosine, 5-fluorouracil, 5-bromouracil, pseudoisocytosine, 2-hydroxy-5-methyl-4-triazolopyridine, isocytosine, isoguanine, inosine, and the "non-naturally occurring" nucleobases described in Benner et al., U.S. Pat. No. 5,432,272 and Susan M. Freier and Karl-Heinz Altmann, Nucleic Acid Research, 25: 4429-4443, 1997. The term "nucleobase" thus includes not only the known purine and pyrimidine heterocycles, but also heterocyclic analogs and tautomers thereof. Further naturally and non naturally occurring nucleobases include those disclosed in U.S. Pat. No. 3,687,808; in chapter 15 by Sanghvi, in Antisense Research and Application, Ed. S. T. Crooke and B. Lebleu, CRC Press, 1993; in Englisch, et al., Angewandte Chemie, International Edition, 30: 613-722, 1991 (see, especially pages 622 and 623, and in the Concise Encyclopedia of Polymer Science and Engineering, J. I. Kroschwitz Ed., John Wiley & Sons, pages 858-859, 1990, Cook, Anti-Cancer Drug Design 6: 585-607, 1991, each of which are hereby incorporated by reference in their entirety). The term also encompasses universal bases, e.g., a 3-nitropyrrole or a 5-nitroindole. Other preferred nucleobases include pyrene and pyridyloxazole derivatives, pyrenyl, pyrenylmethylglycerol derivatives, and the like. Other preferred universal bases include, pyrrole, diazole, or triazole derivatives, including those universal bases known in the art. Further exemplary modified bases are described in Guckian, et al., J. Am. Chem. Soc., 122: 2213-2222, 2000, EP 1 072 679 and WO 97/12896.

When two different, non-overlapping oligonucleotides anneal to different regions of the same linear complementary nucleic acid sequence, the 3' end of one oligonucleotide points toward the 5' end of the other; the former may be called the "upstream" oligonucleotide and the latter the "downstream" oligonucleotide. The complement of a nucleic acid sequence as used herein refers to an oligonucleotide which, when aligned with the nucleic acid sequence such that the 5' end of one sequence is paired with the 3' end of the other, is in "antiparallel association." Complementarity may not be perfect; stable duplexes may contain mismatched base pairs or unmatched bases. Those skilled in the art of nucleic acid technology can estimate duplex stability empirically considering a number of variables including, for example, the length of the oligonucleotide, percent concentration of cytosine and guanine bases in the oligonucleotide, ionic strength, and incidence of mismatched base pairs.

Stability of a nucleic acid duplex is measured by the melting temperature, or "$T_m$". The $T_m$ of a particular nucleic acid duplex under specified conditions is the temperature at which half of the duplexes have disassociated.

The term nucleic acid further encompasses LNA and PNA. Other modifications of the backbone include internucleotide linkers of 2 to 4, desirably 3, groups/atoms selected from —$CH_2$—, —O—, —S—, —$NR^H$—, >C=O, >C=$NR^H$, >C=S, —Si(R")$_2$—, —SO—, —S(O)$_2$—, —P(O,O$^-$)—, —P(O,OH)—, —PO(BH$_3$)—, —P(O,S$^-$)—, —P(O,SH)—, —P(S,O$^-$)—, —P(S,OH)—, P(S,S$^-$)—, —P(S,SH)—, —PO(R")—, —PO(OCH$_3$)—, and —PO($NH^H$)—, where $R^H$ is selected from hydrogen and $C_{1-4}$-alkyl, and R" is selected from $C_{1-6}$-alkyl and phenyl. Other linkers include —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH=, —$CH_2$—$CH_2$—O—, —$NR^H$—$CH_2$—$CH_2$—, —$CH_2$—$CH_2$—$NR^H$—, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C(=$NR^H$)—$NR^H$—, —$NR^H$—CO—$CH_2$—$NR^H$—, O—CO—O—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N=, —$CH_2$—O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$—, —O—$CH_2$—S—, —S—$CH_2$—O—, —$CH_2$—$CH_2$—S—, —O—$CH_2$—$CH_2$—S—, —S—$CH_2$—CH=, —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—$SO_2$—$CH_2$—, —O—SO—O—, —O—S(O)$_2$—O—, —O—S(O)$_2$—$CH_2$—, —O—S(O)$_2$—$NR^H$—, —$NR^H$—S(O)$_2$—$CH_2$—, —O—S(O)$_2$—$CH_2$—, —O—P(O,OH)—O—, —O—P(O,O$^-$)—O—, —O—P(O,SH)—O—, —O—P(O,S$^-$)—O—, O—P(S,OH)—O—, —O—P(S,O$^-$)—O—, —O—P(S,SH)—O—, —O—P(S,S$^-$)—O—, —S—P(O, OH)—O—, —S—P(O,O⁻)—O—, —S—P(O,SH)—O—, —S—P(O,S⁻)—O—, —S—P(S,OH)—O—, —S—P(S,O⁻)—O—, —S—P(S,S⁻)—O—, —S—P(S,SH)—O—, —O—P(O,O⁻)—S—, O—P(O,OH)—S—, —O—P(O,SH)—S—, —O—P(O,S⁻)—S—, —O—P(S,OH)—S—, —O—P(S,O⁻)—S—, —O—P(S,SH)—S—, —O—P(S,S⁻)—S—, —S—P(O,O⁻)—S—, —S—P(O,OH)—S—, —S—P(O,SH)—S—, —S—P(O,S⁻)—S—, S—P(S,OH)—S—, —S—P(S,O⁻)—S—, —S—P(S,SH)—S—, —S—P(S,S⁻)—S—, —O—PO(R")—O—, —O—PO(OCH$_3$)—O—, —O—PO(OCH$_2$CH$_3$)—O—, —O—PO(OCH$_2$CH$_2$SR)—O—, —O—PO(BH$_3$)—O—, —O—PO(NHR$^N$)—O—, —O—P(O)$_2$—NR$^H$—, —NR$^H$—P(O,OH)—O—, —O—P(O,NR$^H$)—O—, —CH$_2$—P(O,OH)—O—, —O—P(O,OH)—CH$_2$—, and —O—Si(R")$_2$—O—; among which —CH$_2$—CO—NR$^H$—, —CH$_2$—NR$^H$—O—, —S—CH$_2$—O—, —O—P(O,OH)—O—, —O—P(O,SH)—O—, —O—P(S,SH)—O—, —NR$^H$—P(O,OH)—O—, —O—P(O,NR$^H$)—O—, —O—PO(R")—O—, —O—PO(CH$_3$)—O—, and —O—PO(NHR$^N$)—O—, where R$^H$ is selected from hydrogen and C$_{1-4}$-alkyl, and R" is selected from C$_{1-6}$-alkyl and phenyl. Further illustrative examples are given in Mesmaeker et. al., Current Opinion in Structural Biology 1995, 5, 343-355 and Susan M. Freier and Karl-Heinz Altmann, Nucleic Acids Research, 1997, vol 25, pp 4429-4443. The left-hand side of the internucleoside linkage is bound to the 5-membered ring at the 3'-position, whereas the right-hand side is bound to the 5'-position of a preceding monomer.

Additionally, the nucleic acids may be modified at either the 3' and/or 5' end by any type of modification known in the art. For example, either or both ends may be capped with a protecting group, attached to a flexible linking group, attached to a reactive group to aid in attachment to the substrate surface, etc.

Exemplary 5', 3', and/or 2' terminal groups include —H, —OH, halo (e.g., chloro, fluoro, iodo, or bromo), optionally substituted aryl, (e.g., phenyl or benzyl), alkyl (e.g., methyl or ethyl), alkoxy (e.g., methoxy), acyl (e.g., acetyl or benzoyl), aroyl, aralkyl, hydroxy, hydroxyalkyl, alkoxy, aryloxy, aralkoxy, nitro, cyano, carboxy, alkoxycarbonyl, aryloxycarbonyl, aralkoxycarbonyl, acylamino, aroylamino, alkylsulfonyl, arylsulfonyl, heteroarylsulfonyl, allylsulfinyl, arylsulfinyl, heteroarylsulfinyl, alkylthio, arylthio, heteroarylthio, aralkylthio, heteroaralkylthio, amidino, amino, carbamoyl, sulfamoyl, alkene, alkyne, protecting groups (e.g., silyl, 4,4'-dimethytrityl, monomethoxytrityl, or trityl(triphenylmethyl)), linkers (e.g., a linker containing an amine, ethylene glycol, quinone such as anthraquinone), detectable labels (e.g., radiolabels or fluorescent labels), and biotin.

By "LNA" is meant locked nucleic acid. LNA monomers as disclosed in PCT Publication WO 99/14226 are in general particularly desirable for use in the invention. Desirable LNA monomers and their method of synthesis also are disclosed in U.S. Pat. Nos. 6,043,060, 6,268,490, PCT Publications WO 01/07455, WO 01/00641, WO 98/39352, WO 00/56746, WO 00/56748 and WO 00/66604 as well as in the following papers: Morita et al., Bioorg. Med. Chem. Lett. 12(1):73-76, 2002; Hakansson et al., Bioorg. Med. Chem. Lett. 11(7):935-938, 2001; Koshkin et al., J. Org. Chem. 66(25):8504-8512, 2001; Kvaerno et al., J. Org. Chem. 66(16):5498-5503, 2001; Halkansson et al., J. Org. Chem. 65(17):5161-5166, 2000; Kvaerno et al., J. Org. Chem. 65(17):5167-5176, 2000; Pfundheller et al., Nucleosides Nucleotides 18(9):2017-2030, 1999; and Kumar et al, Bioorg. Med. Chem. Lett. 8(16):2219-2222, 1998.

When at least two LNA nucleotides are included in the oligonucleotide composition, these may be consecutive or separated by one or more non-LNA nucleotides. In one aspect, LNA nucleotides are alpha-L-LNA and/or xylo LNA nucleotides as disclosed in PCT Publications No. WO 2000/66604 and WO 2000/56748. Preferred LNA monomers, also referred to as "oxy-LNA" are LNA monomers which include bicyclic compounds as disclosed in PCT Publication WO 03/020739 wherein the bridge between the 2' and 4' positions is —CH$_2$—O— or —CH$_2$—CH$_2$—O—. Preferred LNA monomers, also referred to as "amino-LNA," are LNA monomers which include bicyclic compounds as claimed in U.S. Pat. Nos. 6,794,499 or 6,670,461 as well as disclosed in the following papers: Singh et al, J. Org. Chem. 1998, 63, 6078-9, Singh et al, J. Org. Chem. 1998, 63, 10035-9 and Rosenbohm et al, Org. Biomol. Chem., 2003, 1, 655-663.

It is understood that references herein to a nucleic acid unit, nucleic acid residue, LNA monomer, or similar term are inclusive of both individual nucleoside units and nucleotide units and nucleoside units and nucleotide units within an oligonucleotide.

The term "target nucleic acid" refers to any relevant nucleic acid of a single specific sequence, e.g., a biological nucleic acid, e.g., derived from a patient, an animal (a human or non-human animal), a plant, a bacteria, a fungi, an archae, a cell, a tissue, another organism, etc. It is recognized that the target nucleic acids can be derived from essentially any source of nucleic acids (e.g., including, but not limited to chemical syntheses, amplification reactions, forensic samples, etc.). It is either the presence or absence of one or more target nucleic acids that is to be detected, or the amount of one or more target nucleic acids that is to be quantified. The target nucleic acid(s) that are detected preferentially have nucleotide sequences that are complementary to the nucleic acid sequences of the corresponding probe(s) to which they specifically bind (hybridize). The term target nucleic acid may refer to the specific subsequence of a larger nucleic acid to which the probe specifically hybridizes, or to the overall sequence (e.g., gene or mRNA) whose abundance (concentration) and/or expression level it is desired to detect. The difference in usage will be apparent from context. "Target sequence" refers to a specific nucleic acid sequence within any target nucleic acid.

The term "stringent conditions" refers to conditions under which a probe will hybridize preferentially to its target sequence, and to a lesser extent to, or not at all to, other sequences. Stringent conditions are sequence-dependent and will be different in different circumstances. Longer sequences hybridize specifically at higher temperatures. Generally, stringent conditions are selected to be about 5° C. lower than the thermal melting point (T$_m$) for the specific sequence at a defined ionic strength and pH. The T$_m$ is the temperature (under defined ionic strength, pH, and nucleic acid concentration) at which 50% of the probes complementary to the target sequence hybridize to the target sequence at equilibrium. (As the target sequences are generally present in excess, at T$_m$, 50% of the probes are occupied at equilibrium). Typically, stringent conditions will be those in which the salt concentration is at least about 0.01 to 1.0 M Na ion concentration (or other salts) at pH 7.0 to 8.3, and the temperature is at least about 30° C. for short probes (e.g., 10 to 50 nucleotides). Stringent conditions may also be achieved with the addition of destabilizing agents such as formamide. Hybridization techniques are generally described in Nucleic Acid Hybridization, A Practical Approach, Ed. Hames, B. D. and Higgins, S. J., IRL Press, 1985; Gall and Pardue, Proc. Natl. Acad. Sci., USA 63: 378-383, 1969; and John, et al. Nature 223: 582-587, 1969.

The present invention also contemplates sample preparation methods in certain preferred embodiments. For example, see the patents in the gene expression, profiling, genotyping and other use patents herein, as well as U.S. Ser. No. 09/854,317, Wu and Wallace, Genomics 4, 560 (1989), Landegren et al., Science 241, 1077 (1988), Burg, U.S. Pat. Nos. 5,437,990, 5,215,899, 5,466,586, 4,357,421, Gubler et al., 1985, Biochemica et Biophysica Acta, Displacement Synthesis of Globin Complementary DNA: Evidence for Sequence Amplification, transcription amplification, Kwoh et al., Proc. Natl. Acad. Sci. USA 86, 1173 (1989), Guatelli et al., Proc. Nat. Acad. Sci. USA, 87, 1874 (1990), WO 88/10315, WO 90/06995, and U.S. Pat. No. 6,361,947.

The present invention also contemplates detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625 and in PCT Application PCT/US99/06097 (published as WO99/47964), each of which also is hereby incorporated by reference in its entirety for all purposes.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, Biochemistry, (W H Freeman), Gait, "Oligonucleotide Synthesis: A Practical Approach" 1984, IRL Press, London, all of which are herein incorporated in their entirety by reference for all purposes.

Other features and advantages will be apparent from the following description and the claims.

DETAILED DESCRIPTION OF THE INVENTION

The invention features reagents for labelling nucleic acids, nucleic acids so labelled, and methods of using the reagents, e.g., in detection or quantification of target nucleic acids.

In particular, the invention features a reagent having the formula:

or a salt thereof, wherein B is a nucleobase; $R^2$ is a functional group that permits attachment of the reagent, e.g., via ligation, to a 3' OH group of a nucleic acid, e.g., RNA; L is a linker group; and $R^1$ is a detectable moiety.

Exemplary nucleobases include adenine (A), guanine (G), cytosine (C), thymine (T) and uracil (U) as well as non-naturally occurring nucleobases such as xanthine, diaminopurine, 8-oxo-$N^6$-methyladenine, 7-deazaxanthine, 7-deazaguanine, $N^4,N^4$-ethanocytosine, $N^6,N^6$-ethano-2,6-diaminopurine, 5-methylcytosine (also termed "mC"), 5-($C^3$-$C^6$)-alkynyl-cytosine, 5-fluorouracil, 5-bromouracil, pseudoisocytosine, 2-hydroxy-5-methyl-4-triazolopyridine, isocytosine, isoguanine, inosine, universal bases, e.g., a 3-nitropyrrole or a 5-nitroindole, pyrene and pyridyloxazole derivatives, pyrenyl, pyrenylmethylglycerol derivatives, and pyrrole, diazole, or triazole derivatives. Other nucleobases are described in Benner et al., U.S. Pat. No. 5,432,272; Susan M. Freier and Karl-Heinz Altmann, Nucleic Acid Research, 25: 4429-4443, 1997; U.S. Pat. No. 3,687,808; chapter 15 by Sanghvi, in Antisense Research and Application, Ed. S. T. Crooke and B. Lebleu, CRC Press, 1993; Englisch, et al., Angewandte Chemie, International Edition, 30: 613-722, 1991 (see, especially pages 622 and 623, the Concise Encyclopedia of Polymer Science and Engineering, J. I. Kroschwitz Ed., John Wiley & Sons, pages 858-859, 1990, Cook, Anti-Cancer Drug Design 6: 585-607, 1991; Guckian, et al., Journal of the American Chemical Society, 122: 2213-2222, 2000; EP 1 072 679; and WO 97/12896. A preferred base is 5-methylcytosine. Other preferred bases include the naturally occurring bases A, T, G, C, and U.

Exemplary groups for $R^2$ include phosphate, diphosphate, triphosphate, and corresponding thiophosphate groups. Another $R^2$ is a nucleoside pyrophosphate, resulting in a NppB structure).

Exemplary linkers include the residue of a $C_{1-10}$ alkyl amine after reaction with $R^1$, resulting, e.g., in an amide group. Other amine-reactive detectable moieties are well known in the art.

Exemplary detectable moieties include fluorophores and biotin, as described herein.

It is understood that any particular group of the reagent or a nucleic acid may or may not be ionized, e.g., in free acid, free base, or salt form, depending on the chemical environment.

Labelling

The reagents of the application are preferably used to label nucleic acids, e.g., found in a sample. Use of the reagent for labelling renders the labelled nucleic acid detectable by one or more techniques. Labelling may provide signals detectable by fluorescence, radioactivity, colorimetric, X-ray diffraction or absorption, magnetism, enzymatic activity, and the like or may provide recognition sites for labelling reagents such as antibodies or nucleic acids having detectable labels ("indirect detection").

The reagent may be incorporated by any of a number of means well known to those of skill in the art. However, in a preferred embodiment, the reagent is simultaneously incorporated during the amplification step in the preparation of the sample nucleic acids. For example, polymerase chain reaction (PCR) with reagent-labelled primers or reagent-labelled nucleotides will provide a reagent-labelled amplification product. The nucleic acid (e.g., DNA) may also be amplified in the presence of a reagent-labelled deoxynucleotide triphosphates (dNTPs).

Alternatively, a reagent may be added directly to the original nucleic acid sample (e.g., mRNA, polyA mRNA, cDNA, etc.) or to the amplification product after the amplification is completed. Such labelling can result in the increased yield of amplification products and reduce the time required for the amplification reaction. Means of attaching reagents to nucleic acids include, for example nick translation or end-labelling (e.g., with a labelled RNA) by kinasing of the nucleic acid and subsequent attachment (ligation) of a nucleic acid linker joining the sample nucleic acid to a reagent (e.g., that is fluorescent).

In many applications, it is useful to label nucleic acid samples directly without having to go through amplification, transcription, or other nucleic acid conversion steps. This is especially true for monitoring of mRNA levels where one would like to extract total cytoplasmic RNA or poly A+ RNA (mRNA) from cells and hybridize this material without any intermediate steps. See U.S. Pat. No. 6,344,316, which is hereby incorporated by reference in its entirety for all purposes.

End labelling can be performed using terminal transferase (TdT). End labelling can also be accomplished by ligating a reagent or reagent-labelled nucleotide or nucleic acid to the end of a target nucleic acid or probe. See U.S. Pat. No. 6,344,316. Thus, according to one aspect of the present invention, where the nucleic acid is an RNA, a labelled ribonucleotide can be ligated to the RNA using an RNA ligase. RNA ligase catalyzes the covalent joining of single-stranded RNA (or DNA, but the reaction with RNA is more efficient) with a 5' phosphate group to the 3'-OH end of another piece of RNA (or DNA). The specific requirements for the use of this enzyme are described in The Enzymes, Volume XV, Part B, T4 RNA Ligase, Uhlenbeck and Greensport, pages 31-58; and 5.66-5.69 in Sambrook et al., Molecular Cloning, A Laboratory Manual, Cold Spring Harbor Press, Cold Spring Harbor, N.Y. (1982), all of which are incorporated here by reference in full.

In accordance with one aspect of the present invention, an RNA labelling compound can be directly ligated to the '3-OH group of an RNA molecule without any processing of the molecule. For example, microRNAs (miRNAs) are an extensive class of small noncoding RNAs (approximately 15-25 nucleotides). It is believed that these RNAs play a role in the regulation of gene expression. For example, in C. elegans, lin-4 and let-7 miRNAs control the timing of fate specification of neuronal and hypodermal cells during larval development. (Lagos-Quintana M, Rauhut R, Lendeckel W, Tuschl T. Science 2001, 294:853-858.) The enzymatic machinery involved in the biogenesis of miRNAs in plants and animals has also been extensively studied. For example, RNAse type III-like Dicer, together with Argonaute proteins, cleaves a miRNA hairpin precursor (70 to 75 nucleotides) to yield a stable, about 22 nucleotide miRNA from one arm of the hairpin. (Ke X S, Liu C M, Liu D P, Liang C C. Curr Opin Chem Biol 2003, 7:516-523.)

miRNAs have free 3' OH groups. Hence, the reagents of the instant invention can be directly ligated onto the end of such RNAs without pre-fragmentation or dephosphorylation as may be required for mRNA or cRNA.

RNA can be randomly fragmented with heat in the presence of $Mg^{2+}$. This generally produces RNA fragments with 5' OH groups and phosphorylated 3' ends. Alkaline phosphatase, e.g., calf intestinal alkaline phosphatase (CIAP) as described in U.S. Pat. No. 5,523,221, may be used to remove the phosphate group from the 3' ends of the RNA fragment. A reagent of the invention is then ligated to the 3' OH group of the RNA fragments using T4 RNA ligase to provide a labelled RNA. RNaseIII may also be employed to fragment RNA.

T4 RNA ligase is one enzyme that may be used to enzymatically incorporate a reagent into an RNA or fragmented RNA population. T4 RNA ligase catalyzes ligation of a 5' phosphoryl-terminated nucleic acid donor to a 3' hydroxyl-terminated nucleic acid acceptor through the formation of a 3' to 5' phosphodiester bond, with hydrolysis of ATP to AMP and PPi. Although the minimal acceptor must be a trinucleoside diphosphate, dinucleoside pyrophosphates (NppN) and mononucleoside 3',5'-disphosphates (pNp) are effective donors in the intermolecular reaction. See, for example, Richardson, R. W. and Gumport, R. I. (1983), Nuc. Acid Res: 11, 6167-6185, England, T. E., Bruce, A. G., and Uhlenbeck, O. C. (1980), Meth. Enzymol 65, 65-74, and Hoffmann and McLaughlin, Nuc. Acid. Res. 15, 5289-5303 (1987), which are hereby incorporated by reference in its entirety for all purposes. Reaction conditions may be adjusted to provide optimal conditions for T4 RNA ligase function and may improve efficiency of the ligase reaction. Adjustments may include changing in concentration of buffer constituents or addition of adjuvant compositions such as DMSO, PEG, or other compounds to increase ligase efficiency.

Methods

The invention features methods of detecting nucleic acids labelled with the reagents provided herein. The detection may be quantitative or qualitative and may be potentially used with any nucleic acid. In a preferred embodiment, the methods are used to detect the amount of reagent-labelled nucleic acid that is hybridized to a complementary sequence. For example, the extent of hybridization to an array may be determined.

Detection of nucleic acids may be used for gene expression monitoring, profiling, library screening, genotyping, and diagnostics. Gene expression monitoring, and profiling methods can be shown in U.S. Pat. Nos. 5,800,992, 6,013,449, 6,020,135, 6,033,860, 6,040,138, 6,177,248 and 6,309,822. Genotyping and uses therefor are shown in U.S. Ser. No. 10/013,598, and U.S. Pat. Nos. 5,856,092, 6,300,063, 5,858, 659, 6,284,460 and 6,333,179. Other uses are embodied in U.S. Pat. Nos. 5,871,928, 5,902,723, 6,045,996, 5,541,061, and 6,197,506.

The information obtained from detection may then be used for any suitable purpose. For example, selecting an organism out of a population based upon detection of the target nucleic acid. When the target nucleic acid is derived from a patient, e.g., a human patient, selecting a treatment, diagnosing a disease, or diagnosing a genetic predisposition to a disease, may be based upon detection of the target nucleic acid.

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label or moiety. It is generally recognized that nucleic acids are denatured by increasing the temperature or decreasing the salt concentration of the buffer containing the nucleic acids, or in the addition of chemical agents, or the raising of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe). Shorter probes (e.g., 8-mers) discriminate mismatches very well, but the overall duplex stability is low.

Altered duplex stability conferred by using oligonucleotide or polynucleotide analog probes can be ascertained by following, e.g., fluorescence signal intensity of oligonucleotide or polynucleotide analog arrays hybridized with a target oligonucleotide or polynucleotide over time. The data allow optimization of specific hybridization conditions at, e.g., room temperature (for simplified diagnostic applications in the future).

Another way of verifying altered duplex stability is by following the signal intensity generated upon hybridization with time. Previous experiments using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of the best conditions at a specified temperature. Methods of optimizing hybridization conditions are well known to those of skill in the art (see, e.g., Laboratory Techniques in Biochemistry and Molecular Biology, Vol. 24: Hybridization With Nucleic Acid Probes, P. Tijssen, ed. Elsevier, N.Y., (1993)).

One of skill in the art will appreciate that hybridization conditions may be selected to provide any degree of stringency. In a preferred embodiment, hybridization is performed at low stringency, in this case in 6×SSPE-T at about 40° C. to about 50° C. (0.005% Triton X-100) to ensure hybridization, and then subsequent washes are performed at higher stringency (e.g., 1×SSPE-T at 37° C.) to eliminate mismatched hybrid duplexes. Successive washes may be performed at increasingly higher stringency (e.g., down to as low as 0.25× SSPE-T at 37° C. to 50° C.) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in a preferred embodiment, the wash is performed at the highest stringency that produces consistent results and that provides a signal intensity that is at least 10% greater than the background.

Thus, in a preferred embodiment, a hybridized array may be washed at successively higher stringency solutions and read between each wash. Analysis of the data sets thus produced will reveal a wash stringency above which the hybridization pattern is not appreciably altered and which provides adequate signal for the particular probes of interest.

In a preferred embodiment, background signal is reduced by the use of a detergent (e.g., C-TAB) or a blocking reagent (e.g., sperm DNA, cot-1 DNA, etc.) during the hybridization to reduce non-specific binding. In a particularly preferred embodiment, the hybridization is performed in the presence of about 0.1 to about 0.5 mg/ml DNA (e.g., herring sperm DNA). The use of blocking agents in hybridization is well known to those of skill in the art (see, e.g., Chapter 8 in Laboratory Techniques in Biochemistry and Molecular Biology, Vol. 24: Hybridization With Nucleic Acid Probes, P. Tijssen, ed. Elsevier, N.Y., (1993))

Nucleic Acids

The reagents and methods of the invention may be employed with any nucleic acid, e.g., DNA, RNA, hybrids, and analogs. Nucleic acids that are labelled with the reagents of the invention or that hybridize with such nucleic acids may include any of the nucleobases discussed herein. Examples include genomic DNA or RNA, cDNA, semi synthetic DNA or RNA, or synthetic DNA or RNA, nucleic acids including analogs of natural nucleotides that can function in a similar manner as naturally occurring nucleotides, and nucleic acids having modified backbones. Exemplary types of RNA that are labelled or detected include total RNA, miRNA, cRNA, mRNA, and siRNA. Nucleic acids may also be LNA or PNA. In a preferred embodiment, the nucleic acid that is labelled or to which a labelled nucleic acid hybridizes includes at least one LNA monomer or another high affinity nucleotide monomer. Nucleic acids that are not labelled with a reagent of the invention may be labelled or otherwise chemically altered as is well known in the art. Detection of hybridization between nucleic acids that have both been labelled with a reagent of the invention, e.g., with the same or different detectable moieties, is also encompassed by the invention.

Arrays

The nucleic acid molecules described herein (e.g., detectably labelled microRNAs that are amplified from a sample or that include a linker, or a nucleic acid molecule as such), or fragments thereof, are useful as hybridizable array elements in a microarray. The array elements are organized in an ordered fashion such that each element is present at a specified location on the substrate. Useful substrate materials include membranes, composed of paper, nylon or other materials, filters, chips, beads, glass slides, and other solid supports. The ordered arrangement of the array elements allows hybridization patterns and intensities to be interpreted as expression levels of particular genes or proteins.

Alternatively, an array element is identified not by its geographical location, but because it is linked to an identifiable substrate. The substrate would necessarily have a characteristic (e.g., size, color, fluorescent label, charge, or any other identifiable signal) that allows the substrate and its linked nucleic acid molecule to be distinguished from other substrates with linked nucleic acid molecules. The association of the array element with an identifiable substrate allows hybridization patterns and intensities to be interpreted as expression levels of particular genes. In one example, a nucleic acid molecule is affixed to a bead that fluoresces at a particular wavelength. Binding of a reagent-labelled microRNA to the oligonucleotide may alter the fluorescence of the bead, and such binding can be detected using standard methods.

Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, and 6,136,269, in PCT Applications Nos. PCT/US99/00730 (International Publication Number WO 99/36760) and PCT/US 01/04285, and in U.S. patent application Ser. Nos. 09/501,099 and 09/122,216 which are all incorporated herein by reference in their entirety for all purposes. Preferred arrays are commercially available from Exiqon, Inc. (Boston).

Patents that describe synthetic techniques in specific embodiments include U.S. Pat. Nos. 5,412,087, 6,147,205, 6,262,216, 6,310,189, 5,889,165, and 5,959,098.

Detectable Moieties

A detectable moiety provides a signal either directly or indirectly. A direct signal is produced where the moiety spontaneously emits a signal, or generates a signal upon the introduction of a suitable stimulus. Radiolabels, such as $^{3}H$, $^{125}I$, $^{35}S$, $^{14}C$, or $^{32}P$, and magnetic particles, such as Dynabeads™, are nonlimiting examples of groups that directly and spontaneously provide a signal. Labelling groups that directly provide a signal in the presence of a stimulus include the following nonlimiting examples: colloidal gold (40-80 nm diameter), which scatters green light with high efficiency; fluorescent labels, such as fluorescein, texas red, rhodamine, and green fluorescent protein (Molecular Probes, Eugene, Oreg.), which absorb and subsequently emit light; chemiluminescent or bioluminescent labels, such as luminol, lophine, acridine salts, and luciferins, which are electronically excited as the result of a chemical or biological reaction and subsequently emit light; spin labels, such as vanadium, copper, iron, manganese, and nitroxide free radicals, which are detected by electron spin resonance (ESR) spectroscopy; dyes, such as quinoline dyes, triarylmethane dyes, and acridine dyes, which absorb specific wavelengths of light; and colored glass or plastic (e.g., polystyrene, polypropylene, latex, etc.) beads. See U.S. Pat. Nos. 3,817,837; 3,850,752; 3,939,350; 3,996,345; 4,277,437; 4,275,149, and 4,366,241.

A detectable moiety provides an indirect signal where it interacts with a second compound that spontaneously emits a signal, or generates a signal upon the introduction of a suitable stimulus.

Biotin is particularly preferred detectable moiety. Biotin produces a signal by forming a conjugate with streptavidin (or avidin), which is then detected. See Hybridization With Nucleic Acid Probes. In Laboratory Techniques in Biochemistry and Molecular Biology; Tijssen, P., Ed.; Elsevier: New York, 1993; Vol. 24. An enzyme, such as horseradish peroxidase or alkaline phosphatase, that is attached to an antibody in a label-antibody-antibody as in an ELISA assay, also produces an indirect signal. Another indirect detectable moiety is digoxigenin.

In preferred embodiments, multiple detectable moieties are incorporated into the reagent. In particularly preferred embodiments of the present invention, multiple biotin groups may act to boost or enhance the ability of the detectable moiety to be detected.

Indirect detectable moieties may also include ligands, i.e., something that binds. Ligands include functional groups such as: aromatic groups (such as benzene, pyridine, naphthalene, anthracene, and phenanthrene), heteroaromatic groups (such as thiophene, furan, tetrahydrofuran, pyridine, dioxane, and pyrimidine), carboxylic acids, carboxylic acid esters, carboxylic acid halides, carboxylic acid azides, carboxylic acid hydrazides, sulfonic acids, sulfonic acid esters, sulfonic acid halides, semicarbazides, thiosemicarbazides, aldehydes, ketones, primary alcohols, secondary alcohols, tertiary alcohols, phenols, alkyl halides, thiols, disulfides, primary amines, secondary amines, tertiary amines, hydrazines, epoxides, maleimides, $C_1$-$C_{20}$ alkyl groups optionally interrupted or terminated with one or more heteroatoms such as oxygen atoms, nitrogen atoms, and/or sulfur atoms, optionally containing aromatic or mono/polyunsaturated hydrocarbons, polyoxyethylene such as polyethylene glycol, oligo/polyamides such as poly-β-alanine, polyglycine, polylysine, peptides, oligo/polysaccharides, oligo/polyphosphates, toxins, antibiotics, cell poisons, and steroids, and also "affinity ligands", i.e., functional groups or biomolecules that have a specific affinity for sites on particular proteins, antibodies, poly- and oligosaccharides, and other biomolecules.

A preferred detectable moiety is a fluorescent group. Fluorescent groups typically produce a high signal to noise ratio, thereby providing increased resolution and sensitivity in a detection procedure. Preferably, the fluorescent group absorbs light with a wavelength above about 300 nm, more preferably above about 350 nm, and most preferably above about 400 nm. The wavelength of the light emitted by the fluorescent group is preferably above about 310 nm, more preferably above about 360 nm, and most preferably above about 410 nm.

A fluorescent detectable moiety is selected from a variety of structural classes, including the following nonlimiting examples: 1- and 2-aminonaphthalene, p,p'diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bisbenzoxazole, bis-p-oxazolyl benzene, 1,2-benzophenazine, retinol, bis-3-aminopridinium salts, hellebrigenin, tetracycline, sterophenol, benzimidazolyl phenylamine, 2-oxo-3-chromen, indole, xanthene, 7-hydroxycoumarin, phenoxazine, salicylate, strophanthidin, porphyrins, triarylmethanes, flavin, xanthene dyes (e.g., fluorescein and rhodamine dyes), cyanine dyes, 4,4-difluoro-4-bora-3a,4a-diaza-s-indacene dyes, and fluorescent proteins.

A number of fluorescent compounds are suitable for incorporation into the present invention. Nonlimiting examples of such compounds include the following: dansyl chloride; fluoresceins, such as 3,6-dihydroxy-9-phenylxanthhydrol; rhodamineisothiocyanate; N-phenyl-1-amino-8-sulfonatonaphthalene; N-phenyl-2-amino-6-sulfonatonaphthanlene; 4-acetamido-4-isothiocyanatostilbene-2,2'-disulfonic acid; pyrene-3-sulfonic acid; 2-toluidinonaphthalene-6-sulfonate; N-phenyl, N-methyl 2-aminonaphthalene-6-sulfonate; ethidium bromide; stebrine; auromine-0,2-(9'-anthroyl)palmitate; dansyl phosphatidylethanolamine; N,N'-dioctadecyl oxacarbocyanine; N,N'-dihexyl oxacarbocyanine; 4-(3'-pyrenyl)butryate; d-3-aminodesoxy-equilenin; 12-(9'-anthroyl)stearate; 2-methylanthracene; 9-vinylanthracene; 2,2'-(vinylene-p-phenylene)bisbenzoxazole; p-bis[2-(4-methyl-5-phenyl oxazolyl)]benzene; 6-dimethylamino-1,2-benzophenzine; bis(3'-aminopyridinium)-1,10-decandiyl diiodide; sulfonaphthylhydrazone of hellibrigenin; chlorotetracycline; N-(7-dimethylamino-4-methyl-2-oxo-3-chromenyl)maleimide; N-[p-(2-benzimidazolyl)phenyl]maleimide; N-(4-fluoranthyl)maleimide; bis (homovanillic acid); resazurin; 4-chloro-7-nitro-2,1,3-benzooxadizole; merocyanine 540; resorufin; rose Bengal; and 2,4-diphenyl-3(2H)-furanone. Preferably, the fluorescent detectable moiety is a fluorescein or rhodamine dye.

Fluorescent moieties and molecules useful in practicing the present invention include but are not limited to dimethylaminonaphthalene sulfonic acid (dansyl), pyrene, anthracene, nitrobenzoxadiazole (NBD), acridine, and dipyrromethenboron difluoride and derivatives thereof. More specifically, non-limiting examples of fluorescent moieties and molecules useful in practicing the present invention include, but are not limited to: carbocyanine, dicarbocyanine, and other cyanine dyes (e.g., CyDye™ fluorophores, such as Cy3, Cy3.5, Cy5, Cy5.5 and Cy7 from Pharmacia). These dyes have a maximum fluorescence at a variety of wavelengths: green (506 nm and 520 nm), green-yellow (540 nm), orange (570 nm), scarlet (596 nm), far-red (670 nm), and near infrared (694 nm and 767 nm); coumarin and its derivatives (e.g., 7-amino-4-methylcoumarin, aminocoumarin, and hydroxycoumarin); BODIPY dyes (e.g., BODIPY FL, BODIPY 630/650, BODIPY 650/665, and BODIPY TMR); fluorescein and its derivatives (e.g., fluorescein isothiocyanate); rhodamine dyes (e.g., rhodamine, rhodamine green, rhodamine red, tetramethylrhodamine, rhodamine 6G, and lissamine rhodamine B); Alexa dyes (e.g., Alexa Fluor-350, -430, -488, -532, -546, -568, -594, -663, and -660, from Molecular Probes); fluorescent energy transfer dyes (e.g., thiazole orange-ethidium heterodimer, TOTAB, etc.); proteins with luminescent properties, e.g.: phycobiliprotein, green fluorescent protein (GFP) and mutants and variants thereof, including by way of non-limiting example fluorescent proteins having altered wavelengths (e.g., YFP, RFP, etc.). (See Chiesa et al., Biochem. J. 355:1-12 (2001); Sacchetti et al., Biochem. J. 355:1-12 (2000) and Histol. Histopathol. 15:101-107 (1995); and Larrick, J. W. et al., Immunotechnology 1:83-86 (1995)); aequorin and mutants and variants thereof; DsRed protein (Baird et al., Proc Natl. Acad. Sci. USA 97:11984-11989 (2000)), and mutants and variants thereof (see Verkhusha et al., 2001. J. Biol. Chem. 276:29621-29624 (2001); Bevis, B. J. and Glick, B. S., Nat. Biotechnol. 20:83-87 (2002); Terskikh et al., J. Biol. Chem. 277:7633-7636 (2002); Campbell et al., Proc Natl Acad. Sci. USA 99:7877-7882 (2002); and Knop et al., Biotechniques 33:592, 594, 596-598 (2002); and other fluors, e.g., 6-FAM, HEX, TET, F12-dUTP, L5-dCTP, 8-anilino-1-naphthalene sulfonate, ethenoadenosine, ethidium bromide prollavine monosemicarbazide, p-terphenyl, 2,5-diphenyl-1,3,4-oxadiazole, 2,5-diphenyloxazole, p-bis[2-(5-phenyloxazolyl)]benzene, lanthanide chelates, Pacific blue, Cascade blue, Cascade Yellow, Oregon Green, Marina Blue, Texas Red, phycoerythrin, eosins, DANSYL (5-dimethylamino)-1-naphthalenesulfonyl), DOXYL (N-oxyl-4,4-dimethyloxazolidine), PROXYL (N-oxyl-2,2,5, 5-tetramethylpyrrolidine), TEMPO (N-oxyl-2,2,6,6-tetramethylpiperidine), dinitrophenyl, acridines, erythrosine, coumaric acid, umbelliferone, Rox, Europium, Ruthenium, Samarium, and other rare earth metals, and erythrosines; as well as derivatives of any of the preceding molecules and moieties. Fluorophores, and kits for attaching fluorophores to nucleic acids and peptides, are commercially available from, e.g., Molecular Probes (Eugene, Oreg.) and Sigma/Aldrich (St. Louis, Mo.).

A further preferred detectable moiety is Oyster®-556 and Oyster®-656 from Denovo Biolabels GmbH.

Another preferred detectable moiety is colloidal gold. The colloidal gold particle is typically 40 to 80 nm in diameter. The colloidal gold may be attached to a labelling compound in a variety of ways. In one embodiment, the linker moiety of the nucleic acid labelling reagent terminates in a thiol group (—SH), and the thiol group is directly bound to colloidal gold through a dative bond. See Mirkin et al. Nature 1996, 382, 607-609. In another embodiment, it is attached indirectly, for instance through the interaction between colloidal gold conjugates of antibiotin and a biotinylated labelling compound. The detection of the gold labelled compound may be enhanced through the use of a silver enhancement method. See Danscher et al. J Histotech 1993, 16, 201-207.

The nucleic acid samples can all be labelled with a single detectable moiety, for example, a single fluorophore. Alternatively, different nucleic acid samples can be simultaneously hybridized where each nucleic acid sample has a different fluorophore. For instance, one target could have a green fluorophore and a second target could have a red fluorophore. A scanning step will distinguish sites of binding of the red fluorophore from those binding the green fluorophore. Each nucleic acid sample can be analyzed independently from one another.

Another type of fluorescence moiety is a set of fluorescence resonance energy transfer (FRET) moieties, where energy absorbed by one moiety is transferred to another moiety that emits fluorescence. When these moieties are employed, one moiety may be part of a reagent of the invention and attached to one nucleic acid, e.g., in a sample, that is hybridized to a second nucleic acid, e.g., in an array. In such embodiments, the second nucleic acid would be labelled with the second FRET moiety, so that a FRET signal is produced upon hybridization.

EXAMPLES

The invention will now be further illustrated with reference to the following examples. It will be appreciated that what follows is by way of example only and that modifications to detail may be made while still falling within the scope of the invention.

Example 1

Synthesis of a Compound of the Invention

-continued

N-Trifluoroacetyl-6-aminohexanol (1)

6-aminohexanol (11.7 g; 100 mmol) is dissolved in dry dichloromethane (100 mL) and drop wise added ethyl trifluoroacetate (15 g; 105 mmol) in dry dichloromethane (50 mL) (~30 min), and the mixture is stirred overnight. Water (10 ml) is added, and the mixture is stirred for 30 min. The solution is washed with water (2×100 mL), dried (Na$_2$SO$_4$), and concentrated. The residue is redissolved in acetonitrile (100 μL) and concentrated. The residue is placed on vacuum overnight, and a white crystalline solid is obtained. Yield 19 g.

DMT-O-mC(Bz)-O—PO(OCNEt)-O—C6-NHTFA (2)

LNA-mC(Bz) phosphoramidite (4.4 g; 5 mmol) and N-TFA-6-aminohexanol (2.1 g; 10 mmol) are co-evaporated with anh. MeCN (2×100 mL), and the residue is redissolved in anh. DCM (50 mL). DCI (10 mmol; 2.1 g) is added, and the mixture is stirred for 5 h (follow on HPLC). When complete reaction is obtained, 0.2 M I$_2$ (25-30 mL until color is maintained) is added (check on HPLC). The reaction mixture is diluted with sat. aq. NaHCO$_3$ (20 mL), and the phases are separated. The aq. phase is extracted with dichloromethane (20 mL), and the combined organic phases are washed with sat. aq. NaHCO$_3$ (2×40 mL) and brine (40 ml), dried over Na$_2$SO$_4$, and concentrated. The residue is purified on a short silica gel column eluted with MeOH/DCM, and product containing fractions are combined an concentrated. Yield 4.1 g.

HO-mC(Bz)-O—PO(OCNEt)-O—C6-NHTFA (3)

2 (3 g, 3 mmol) is stirred in Deblock solution (100 mL; 3% TCA in DCM), and the reaction is followed on TLC and HPLC. When the reaction has reached more than 95% completion, the reaction is quenched with MeOH (25 mL) and K$_2$HPO$_4$ (100 mL) and stirred for 5 min. The phases are separated, and the organic phase washed with sat. aq. NaHCO$_3$ (2×40 mL) and brine (40 mL) and dried (Na$_2$SO$_4$) and concentrated. The residue is purified on a short column with DCM and MeOH/DCM. Product containing fractions are combined and concentrated. Yield 1.9 g.

(CNEtO)$_2$P(O)O-mC(Bz)-O—PO(OCNEt)-O—C6-NHTFA (4)

Compound 3 (0.70 g, 1 mmol) is co-evaporated with acetonitrile (2×25 mL) and redissolved in anhydrous acetonitrile (10 mL). DCI (450 mg) and bis-cyanoethyl-N,N-diisopropyl phosphoramidite (1 g) are added. The reaction is followed on HPLC. After 5 hours, the reaction is complete, and DCM (100 mL) and sat. NaHCO$_3$ (20 mL) are added. The phases are separated, and the organic phase is washed with sat. NaHCO$_3$ (2×20 mL) and brine (20 mL) and dried (Na$_2$SO$_4$) and concentrated. The residue is purified on a short silica gel column with MeOH/DCM. Product containing fractions are combined and concentrated. Yield 0.8 g.

PO(OH)$_2$—O-mC(Bz)-O—PO(OH)—O—(CH$_2$)$_6$—NH$_2$ (5)

Compound 4 (0.5 g; 0.56 mmol) is dissolved in a mixture of 20% diethylamine in acetonitrile (25 mL), and the mixture is stirred for 20 min. 25% aq. NH$_3$ (50 mL) is added, and the mixture is heated to 60° C. for 3 hours. The mixture is concentrated and dissolved in water (25 mL) and extracted with chloroform (2×10 mL) and then concentrated to ~5 mL. 2%

LiClO$_4$ in acetone (50 mL) is added, and a precipitate is formed, which is isolated by centrifugation and dried. Yield 0.21 g.

NH-Oyster556 (6a)

Compound 5 (10 mg) is dissolved in 0.1M sodium borate buffer pH=8.25 (2 mL). Oyster556 NHS ester is dissolved in DMF (1 mL) and added to the solution, and the mixture is placed at 40° C. for 16 hours. To the mixture is added 2% LiClO$_4$ in acetone (20 mL), and the precipitate is isolated by centrifugation. The residue is purified on HPLC (X-Terra RP18 5 μm 10×100 mm; A: 0.05M TEAAc pH=7.4; B: Acetonitrile; 3 mL/min) 5-40% B in 20 minutes. Yield 3.8 mg.

NH-Oyster656 (6b)

Compound 5 (10 mg) is dissolved in 0.1M sodium borate buffer pH=8.25 (2 mL). Oyster656 NHS ester is dissolved in DMF (1 mL) and added to the solution, and the mixture is placed at 40° C. for 16 hours. To the mixture is added 2% LiClO$_4$ in acetone (20 mL), and the precipitate is isolated by centrifugation. The residue is purified on HPLC (X-Terra RP18 5 μm 10×100 mm; A: 0.05M TEAAc pH=7.4; B: Acetonitrile; 3 mL/min) 5-40% B in 20 minutes. Yield 3 mg.

NH-Biotin (6c)

Compound 5 (10 mg) is dissolved in 0.1M sodium borate buffer pH=8.25 (2 mL). Biotin NHS ester is dissolved in DMF (1 mL) and added to the solution, and the mixture is placed at 40° C. for 16 hours. The mixture is added 2% LiClO$_4$ in acetone (20 mL), and the precipitate is isolated by centrifugation. The residue is purified on HPLC (X-Terra RP18 5 μm 10×100 mm; A: 0.05M TEAAc pH=7.4; B: Acetonitrile; 3 mL/min) 5-70% B in 20 minutes. Yield 2.7 mg Example 2

Labelling of Different RNA Oligonucleotides to Show Absence of Labelling Bias

Experimental

Eight RNA oligonucleotides (EQ16901, EQ16914, EQ16904, EQ16903, EQ16913, EQ16902, EQ18465, EQ18467—see table 1) with different 3'-end nucleotides were labelled with the reagent LNA-methyl-C-Cy3 in a 10 μL labelling reaction for 1 hour at 0° C. Each RNA oligonucleotide was labelled separately in an individual labelling reaction of 1 μM RNA oligonucleotide, 10 μM LNA-methyl-C-Cy3, 2 units/μL of T4 RNA ligase (New England Biolabs), 1×T4 RNA ligase ligation buffer (New England Biolabs), and 10% PEG. The labelling reactions were stopped by incubation at 65° C. for 15 minutes. The 10 μL labelling reaction was mixed with an equal volume of 2×TBE-urea loading buffer without dye (Novex, Invitrogen) and incubated for 3 minutes at 70° C. A volume of 5 μL (2.5 μL loading buffer 2.5 μL ligated sample) was loaded on a 15% TBE-urea polyacrylamide gel (PAGE) (Novex, Invitrogen). Electrophoresis was performed in 1×TBE running buffer at a constant voltage of 180 V for 50-60 minutes. The PAGE was dismantled and stained in a 1× solution of SYBR Gold (Molecular Probes, Invitrogen) in 1×TBE buffer followed by a brief wash in 1×TBE. The gel was analysed on Typhoon laser scanner (GE Healthcare). The scanning was performed with a beam-split of 560 nm using the following filters 1) SYBR Gold filter (540 nm-Fluorescein) with a PMT voltage of 400V. 2) Cy3 filter (580 nm BP30) with a PMT voltage of 300V.

On the obtained gel image, bands representing reaction products were analysed using ImageQuant software to determine band intensity and quantity of the reaction products.

TABLE 1

(SEQ ID Nos: 1-8)

| EQ | Oligo Name | Sequence | 3'-1 and 3'- nucleoside residue |
|---|---|---|---|
| 16901 | hsa-miR-145 | guccaguuuucccagg aaucccuu | uu |
| 16914 | hsa-miR-189 | gugccuacugagcuga uaucagu | gu |
| 16904 | hsa-miR-196a | uagguaguuucauguu guugg | gg |
| 16903 | hsa-miR-10a | uacccuguagauccga auuugug | ug |
| 16913 | hsa-miR-200c | aauacugccgguaau gaugga | ga |
| 16902 | hsa-miR-320 | aaaagcugggugaga gggcgaa | aa |
| 18465 | hsa-miR-106a | aaaagugcuuacagug cagguagc | gc |
| 18467 | hsa-miR-142-5p | cauaaaguagaaagca cuac | ac |

Results

Figure 1:
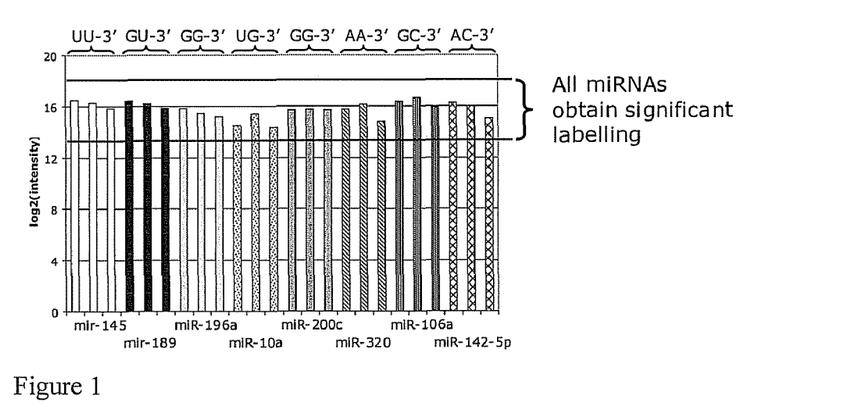
FIG. 1: Quantified signals of ligation products consisting of RNA oligonucleotide ligated to a LNA-methyl-C-Cy3 label. The ligations were performed to 8 different RNA oligonucleotides with sequences identical to the human miRNAs indicated on the x-axis. These 8 miRNAs have different 3'-end nucleoside residues as indicated on the top of the diagram.

FIG. 1 shows the quantified signal of the reaction products consisting of RNA oligonucleotide ligated to the LNA-methyl-C-Cy3 reagent. Since the signal is assumed equal to the amount of reaction product, the conclusion is that the reagent LNA-methyl-C-Cy3 ligates equally well and without bias caused by the type of nucleobases present in the two 3'-end terminal positions of the RNA.

Example 3

Molecular Classification of Breast Cancer by MicroRNA Signatures

Breast cancer is the most frequent form of cancer among women worldwide. Currently, treatment and prognosis is based on clinical and histo-pathological graduation, such as TNM classification (tumor size, lymph node, and distant metastases status) and estrogen receptor status. To improve both the selection of therapy and the evaluation of treatment response, more accurate determinants for prognosis and response, such as molecular tumor markers, are needed. This example probes the expression patterns of microRNAs (miRNAs) in tumors and normal breast tissue to identify new molecular markers of breast cancer.

Biopsies from primary tumors and from the proximal tissue (1 cm from the border zone of tumor) were collected from female patients (age 55-69) undergoing surgery for invasive ductal carcinoma. Total-RNA was extracted following the "Fast RNA GREEN" protocol from Bio110. Assessment of miRNA levels was carried out on Mercury™ microarrays according to the manufacturers recommended protocol (Exiqon, Denmark).

The results from the miRNA analysis revealed numerous differentially expressed miRNAs, including those reported earlier to be associated with breast cancer, such as let-7a/d/f, miR-125a/b, miR-21, miR-32, and miR-136 (Iorio et al., Cancer Research 65(16): 7065-7070, 2005). In addition, we have identified several miRNAs that have not previously been connected with breast cancer.

RNA Extraction:

Before use, all samples were kept at −80° C. Two samples—ca. 100 mg of each—were used for RNA extraction:

PT (primary tumor)

1 C (normal adjacent tissue, one cm from the primary tumor)

The samples were thawed on ice, and kept in RNAlater® (Cat#7020, Ambion) during disruption with a sterile scalpel into smaller ca. 1 mm wide slices.

To a FastPrep GREEN (Cat# 6040-600, Bio101) tube containing lysis matrix was added:

500 µL CRSR-GREEN
500 µL PAR
100 µL CIA
200 µL tissue

The tubes were placed in the FastPrep FP120 cell disrupter (Bio101) and run for 40 seconds at speed 6. This procedure was repeated twice, before cooling on ice for 5 min. The tubes were centrifuged at 4° C. and at maximum speed in an Eppendorf microcentrifuge for 10 min to enable separation into organic and water phases. The upper phase from each vial was transferred to new Eppendorf 1.5 mL tubes while avoiding the interphase. 500 µL CIA was added, vortexed for 10 seconds, and spun at max speed for 2 min to separate the phases. Again, the top phase was transferred to new Eppendorf tubes, while the interphase was untouched. 500 µL DIPS was added, vortexed, and incubated at room temperature for 2 min. The tubes were centrifuged for 5 min at max speed to pellet the RNA. The pellet was washed twice with 250 µL SEWS and left at room temperature for 10 min to air dry. 50 µL SAFE was added to dissolve the pellet, which was stored at −80° C. until use. QC of the RNA was performed with the Agilent 2100 BioAnalyser using the Agilent RNA6000 Nano kit. RNA concentrations were measured in a NanoDrop ND-1000 spectrophotometer. The PT was only 71 ng/µL, so it was concentrated in a speedvac for 15 min to 342 ng/µL. The 1 C was 230 ng/µL and was used as is.

RNA Labelling and Hybridization

Essentially, the instructions detailed in the "miRCURY Array labelling kit Instruction Manual" were followed:

All kit reagents were thawed on ice for 15 min, vortexed and spun down for 10 min. In a 0.6 mL Eppendorf tube, the following reagents were added:

2.5× labelling buffer, 8 µL
Fluorescent label, 2 µL
1 µg total-RNA (2.92 µL (PT) and 4.35 µL (1 C))
Labelling enzyme, 2 µL
Nuclease-free water to 20 µL (5.08 µL (PT) and 3.65 µL (1 C))

Each microcentrifuge tube was vortexed and spun for 10 min. Incubation at 0° C. for 1 hour was followed by 15 min at 65° C., then the samples were kept on ice.

For hybridization, the 12-chamber TECAN HS4800Pro hybridization station was used. 25 µL 2× hybridization buffer was added to each sample, vortexed, and spun. Incubation at 95° C. for 3 min was followed by centrifugation for 2 min. The hybridization chambers were primed with 1× Hyb buffer. 50 µL of the target preparation was injected into the Hyb station and incubated at 60° C. for 16 hours (overnight). The slides were washed at 60° C. for 1 min with Buffer A twice, at 23° C. for 1 min with Buffer B twice, at 23° C. for 1 min with Buffer C twice, at 23° C. for 30 sec with Buffer C once. The slides were dried for 5 min. Scanning was performed in a ScanArray 4000XL (Packard Bioscience).

Results

Figure 2:
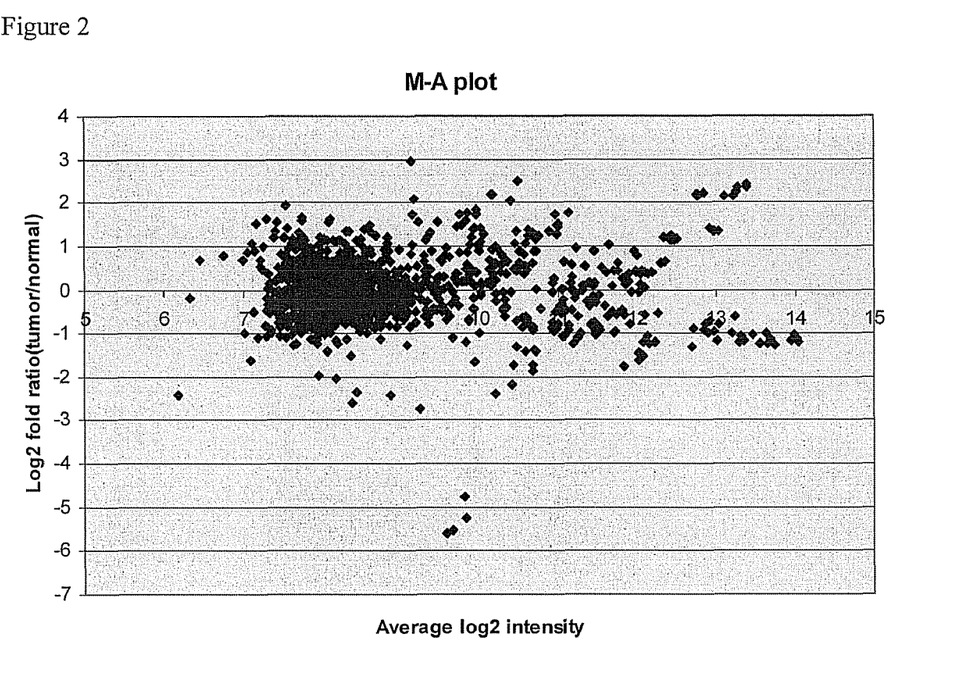
FIG. 2: M-A plot showing all miRNA signals before averaging.

The M-A plot (FIG. 2) shows the Log 2 fold ratio of tumor/normal (M) as a function of the Log 2. In this experiment, a total of 86 out of known 398 miRNAs were found to be differentially expressed between breast cancer and normal adjacent tissue.

Other Embodiments

The present invention has many preferred embodiments and relies on many patents, applications and other references for details known to those of the art. Therefore, when a patent, application, or other reference is cited or repeated herein, it should be understood that it is incorporated by reference in its entirety for all purposes as well as for the proposition that is recited.

Other embodiments are in the claims.

---

What is claimed is:

1. A nucleic acid labelling reagent having the formula:

or an ion thereof, wherein B is a nucleobase; $R^2$ is a functional group that permits attachment to a 3' OH group of a nucleic acid; L is a linker group; and $R^1$ is a detectable moiety.

2. The compound according to claim 1, wherein B is 5-methylcytosine.

3. The compound according to claim 1, wherein $R^2$ is $PO_4^{2-}$, or an acid thereof.

4. The compound according to claim 1, wherein $R^1$ is selected from biotin or a cyanine dye.

5. The compound according to claim 1, wherein L is $C_{1-10}$-alkyl amino, wherein the amino group is bound to $R^1$.

6. The compound according to claim 1, wherein L is —$(CH_2)_6NH$—, wherein the amino group is bound to $R^1$, and $R^2$ is $PO_4^{2-}$, or an acid thereof.

7. The compound according to claim 1, wherein said detectable moiety is detectable by fluorescence, luminescence, optical scattering, optical absorption, radioactivity, X-ray diffraction or absorption, magnetism, or enzymatic activity, or said detectable moiety is an antibody, biotin, or digoxigenin.

8. The compound according to claim 1, wherein $R^2$ is a functional group that permits attachment to a 3' OH group of a nucleic acid by ligation.

9. The compound according to claim 1, wherein said detectable moiety is detectable by fluorescence.

10. A nucleic acid labelling reagent having the formula:

or an ion thereof,
wherein B is 5-methylcytosine; $R^2$ is $PO_4^{2-}$, or an acid thereof; L is —$(CH_2)_6NH$—, wherein the amino group is bound to $R^1$; and $R^1$ is a cyanine dye.

11. A kit comprising a compound of claim 1 and a ligase.

12. The kit according to claim 11, further comprising a nucleic acid array.

13. The kit according to claim 12, wherein said nucleic acid array comprises an LNA.

14. A method of detecting the presence of a nucleic acid of interest, said method comprising the following steps:
(a) providing a sample comprising nucleic acid that may or may not have said nucleic acid of interest;
(b) ligating said nucleic acid in said sample to a nucleic acid labeling reagent of claim 1 to provide labelled nucleic acids;
(c) providing a collection of detection probes directed to said nucleic acid of interest;
(d) contacting the labelled nucleic acids with said collection under hybridizing conditions; and
(e) determining the extent of hybridization of said labelled nucleic acids to said detection probes to determine the presence of said nucleic acid of interest.

15. The method according to claim 14, wherein said nucleic acid of interest is RNA.

16. The method according to claim 15, wherein said RNA comprises miRNA.

17. The method according to claim 14, wherein T4 RNA ligase catalyzes said ligating.

18. The method according to claim 14, wherein said collection of detection probes is a nucleic acid array.

19. The method according to claim 14, wherein said collection of detection probes is immobilized onto one or more solid supports, where each detection probe is present at a specified location on the support.

20. The method according to claim 19, wherein said solid support comprises a bead or a glass slide.

21. The method according to claim 20, wherein said bead has a characteristic that provides for its identification.

22. The method according to claim 14, wherein B is 5-methylcytosine.

23. The method according to claim 14, wherein $R^2$ is $PO_4^{2-}$, or an acid thereof.

24. The method according to claim 14, wherein $R^1$ is selected from biotin or a cyanine dye.

25. The method according to claim 14, wherein L is $C_{1-10}$-alkyl amino, wherein the amino group is bound to $R^1$.

26. The method according to claim 14, wherein L is —$(CH_2)_6NH$—, wherein the amino group is bound to $R^1$, and $R^2$ is $PO_4^{2-}$, or an acid thereof.

27. The method according to claim 14, further comprising contacting said sample with a phosphatase to remove 3' phosphate groups from said nucleic acids in said sample.

28. The method according to claim 14, further comprising adding an adjuvant prior to said ligating.

* * * * *

UNITED STATES PATENT AND TRADEMARK OFFICE
CERTIFICATE OF CORRECTION

| | |
|---|---|
| PATENT NO. | : 8,293,684 B2 |
| APPLICATION NO. | : 11/947724 |
| DATED | : October 23, 2012 |
| INVENTOR(S) | : Mouritzen et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 944 days.

Signed and Sealed this
Twenty-eighth Day of May, 2013

Teresa Stanek Rea
*Acting Director of the United States Patent and Trademark Office*